US009155588B2

(12) United States Patent
Thapliyal et al.

(10) Patent No.: US 9,155,588 B2
(45) Date of Patent: *Oct. 13, 2015

(54) SYSTEM AND METHOD FOR POSITIONING AN ELONGATE MEMBER WITH RESPECT TO AN ANATOMICAL STRUCTURE

(75) Inventors: Hira V. Thapliyal, Los Altos, CA (US); David A. Gallup, Alameda, CA (US); James W. Arenson, Woodside, CA (US); Robert A. Brommer, Fremont, CA (US)

(73) Assignee: VYTRONUS, INC., Sunnyvale, CA (US)

( * ) Notice: Subject to any disclaimer, the term of this patent is extended or adjusted under 35 U.S.C. 154(b) by 750 days.

This patent is subject to a terminal disclaimer.

(21) Appl. No.: 12/480,929

(22) Filed: Jun. 9, 2009

(65) Prior Publication Data
US 2009/0312755 A1 Dec. 17, 2009

Related U.S. Application Data

(60) Provisional application No. 61/061,362, filed on Jun. 13, 2008.

(51) Int. Cl.
*A61B 18/12* (2006.01)
*A61B 18/14* (2006.01)
(Continued)

(52) U.S. Cl.
CPC ........ *A61B 18/1492* (2013.01); *A61M 25/0082* (2013.01); *A61M 25/01* (2013.01); *A61N 7/022* (2013.01); *A61B 18/02* (2013.01);
(Continued)

(58) Field of Classification Search
USPC .................................. 606/41, 27, 34
See application file for complete search history.

(56) References Cited

U.S. PATENT DOCUMENTS 4,641,649 A 2/1987 Walinsky et al.
4,660,571 A * 4/1987 Hess et al. ............... 607/116
(Continued)

FOREIGN PATENT DOCUMENTS

| DE | 10037660 | 2/2002 |
| WO | WO 99/02096 | 1/1999 |
| WO | WO 2005/117734 | 12/2005 |

OTHER PUBLICATIONS

"A new treatment for atrial fibrillation?" Medical Device & Diagnostic Industry, Feb. 2006, p. 30; retrieved from the Internet: <<http://www.devicelink.com/mddi/archive/06/02/013.html>>, 2 pages total.
(Continued)

*Primary Examiner* — Michael Peffley
*Assistant Examiner* — Daniel Fowler
(74) *Attorney, Agent, or Firm* — Wilson Sonsini Goodrich & Rosati

(57) ABSTRACT

Methods and apparatus for an ablation device used in the treatment of atrial fibrillation comprise an elongate shaft and a positioning mechanism adjacent the distal end of the shaft. The positioning mechanism is adapted to facilitate location of an anatomic structure and also to anchor the elongate shaft adjacent the anatomic structure. The positioning mechanism comprises an electrode for stimulating the anatomic structure as well as sensing electrical signals. Also, an energy delivery element is adjacent the distal end of the shaft and is adapted to stimulate the anatomic structure and create a zone of ablation that blocks abnormal electrical activity thereby reducing or eliminating atrial fibrillation in the patient.

26 Claims, 7 Drawing Sheets

(51) Int. Cl.
*A61M 25/00* (2006.01)
*A61M 25/01* (2006.01)
*A61N 7/02* (2006.01)
*A61B 18/02* (2006.01)
*A61B 18/08* (2006.01)
*A61B 18/18* (2006.01)
*A61B 18/00* (2006.01)

(52) U.S. Cl.
CPC ............... *A61B 18/08* (2013.01); *A61B 18/18* (2013.01); *A61B 2018/00029* (2013.01); *A61B 2018/00196* (2013.01); *A61B 2018/00214* (2013.01); *A61B 2018/00279* (2013.01); *A61B 2018/00375* (2013.01); *A61B 2018/00839* (2013.01); *A61B 2018/00898* (2013.01); *A61B 2018/1475* (2013.01); *A61B 2018/1861* (2013.01)

(56) References Cited

U.S. PATENT DOCUMENTS

| | | | |
|---|---|---|---|
| 4,757,820 A | 7/1988 | Itoh | |
| 5,246,438 A | 9/1993 | Langberg | |
| 5,295,484 A | 3/1994 | Marcus et al. | |
| 5,314,466 A | 5/1994 | Stern et al. | |
| 5,405,346 A | 4/1995 | Grundy et al. | |
| 5,471,988 A | 12/1995 | Fujio et al. | |
| 5,718,241 A | 2/1998 | Ben-Haim et al. | |
| 5,735,811 A | 4/1998 | Brisken | |
| 5,916,213 A * | 6/1999 | Haissaguerre et al. | 606/41 |
| 5,957,920 A * | 9/1999 | Baker | 606/33 |
| 6,012,457 A | 1/2000 | Lesh | |
| 6,024,740 A | 2/2000 | Lesh et al. | |
| 6,052,576 A | 4/2000 | Lambourg | |
| 6,064,902 A | 5/2000 | Haissaguerre et al. | |
| 6,117,101 A | 9/2000 | Diederich et al. | |
| 6,123,702 A * | 9/2000 | Swanson et al. | 606/34 |
| 6,161,543 A | 12/2000 | Cox et al. | |
| 6,164,283 A | 12/2000 | Lesh | |
| 6,237,605 B1 | 5/2001 | Vaska et al. | |
| 6,245,064 B1 | 6/2001 | Lesh et al. | |
| 6,245,095 B1 | 6/2001 | Dobak, III et al. | |
| 6,251,129 B1 | 6/2001 | Dobak, III et al. | |
| 6,251,130 B1 | 6/2001 | Dobak, III et al. | |
| 6,254,599 B1 | 7/2001 | Lesh et al. | |
| 6,261,312 B1 | 7/2001 | Dobak, III et al. | |
| 6,277,116 B1 | 8/2001 | Utely et al. | |
| 6,305,378 B1 | 10/2001 | Lesh | |
| 6,311,090 B1 | 10/2001 | Knowlton | |
| 6,311,692 B1 | 11/2001 | Vaska et al. | |
| 6,314,962 B1 | 11/2001 | Vaska et al. | |
| 6,314,963 B1 | 11/2001 | Vaska et al. | |
| 6,379,378 B1 | 4/2002 | Werneth et al. | |
| 6,383,151 B1 | 5/2002 | Diederich et al. | |
| 6,387,089 B1 | 5/2002 | Kreindel et al. | |
| 6,416,511 B1 | 7/2002 | Lesh et al. | |
| 6,468,296 B1 | 10/2002 | Dobak, III et al. | |
| 6,474,340 B1 | 11/2002 | Vaska et al. | |
| 6,475,231 B2 | 11/2002 | Dobak, III et al. | |
| 6,478,811 B1 | 11/2002 | Dobak, III et al. | |
| 6,478,812 B2 | 11/2002 | Dobak, III et al. | |
| 6,484,727 B1 | 11/2002 | Vaska et al. | |
| 6,491,039 B1 | 12/2002 | Dobak, III | |
| 6,491,716 B2 | 12/2002 | Dobak, III et al. | |
| 6,500,121 B1 | 12/2002 | Slayton et al. | |
| 6,500,174 B1 | 12/2002 | Maguire et al. | |
| 6,502,576 B1 | 1/2003 | Lesh | |
| 6,514,244 B2 | 2/2003 | Pope et al. | |
| 6,514,249 B1 * | 2/2003 | Maguire et al. | 606/41 |
| 6,517,536 B2 | 2/2003 | Hooven et al. | |
| 6,529,756 B1 | 3/2003 | Phan et al. | |
| 6,533,804 B2 | 3/2003 | Dobak, III et al. | |
| 6,540,771 B2 | 4/2003 | Dobak, III et al. | |
| 6,542,781 B1 | 4/2003 | Koblish et al. | |
| 6,546,935 B2 | 4/2003 | Hooven | |
| 6,547,788 B1 | 4/2003 | Maguire et al. | |
| 6,551,349 B2 | 4/2003 | Lasheras et al. | |
| 6,576,001 B2 | 6/2003 | Werneth et al. | |
| 6,585,752 B2 | 7/2003 | Dobak, III et al. | |
| 6,592,576 B2 | 7/2003 | Andrews et al. | |
| 6,595,989 B1 | 7/2003 | Schaer | |
| 6,599,288 B2 | 7/2003 | Maguire et al. | |
| 6,602,276 B2 | 8/2003 | Dobak, III et al. | |
| 6,605,084 B2 | 8/2003 | Acker et al. | |
| 6,607,502 B1 | 8/2003 | Maguire et al. | |
| 6,607,527 B1 | 8/2003 | Ruiz et al. | |
| 6,613,046 B1 | 9/2003 | Jenkins et al. | |
| 6,635,054 B2 | 10/2003 | Fjield et al. | |
| 6,645,199 B1 | 11/2003 | Jenkins et al. | |
| 6,645,202 B1 | 11/2003 | Pless et al. | |
| 6,648,908 B2 | 11/2003 | Dobak, III et al. | |
| 6,652,515 B1 | 11/2003 | Maguire et al. | |
| 6,652,517 B1 | 11/2003 | Hall et al. | |
| 6,663,622 B1 * | 12/2003 | Foley et al. | 606/34 |
| 6,666,614 B2 | 12/2003 | Fechter et al. | |
| 6,666,858 B2 | 12/2003 | Lafontaine | |
| 6,669,655 B1 | 12/2003 | Acker et al. | |
| 6,669,687 B1 | 12/2003 | Saadat | |
| 6,676,688 B2 | 1/2004 | Dobak, III et al. | |
| 6,676,689 B2 | 1/2004 | Dobak, III et al. | |
| 6,676,690 B2 | 1/2004 | Werneth | |
| 6,685,732 B2 | 2/2004 | Kramer | |
| 6,689,128 B2 | 2/2004 | Sliwa, Jr. et al. | |
| 6,692,488 B2 | 2/2004 | Dobak, III et al. | |
| 6,695,873 B2 | 2/2004 | Dobak, III et al. | |
| 6,701,931 B2 | 3/2004 | Sliwa, Jr. et al. | |
| 6,702,842 B2 | 3/2004 | Dobak, III et al. | |
| 6,711,444 B2 | 3/2004 | Koblish | |
| 6,719,755 B2 | 4/2004 | Sliwa, Jr. et al. | |
| 6,745,080 B2 | 6/2004 | Koblish | |
| 6,752,805 B2 | 6/2004 | Maguire et al. | |
| 6,758,847 B2 | 7/2004 | Maguire | |
| 6,763,722 B2 | 7/2004 | Fjield et al. | |
| 6,780,183 B2 | 8/2004 | Jimenez, Jr. et al. | |
| 6,786,218 B2 | 9/2004 | Dobak, III | |
| 6,805,128 B1 | 10/2004 | Pless et al. | |
| 6,805,129 B1 | 10/2004 | Pless et al. | |
| 6,814,733 B2 | 11/2004 | Schwartz et al. | |
| 6,840,936 B2 | 1/2005 | Sliwa, Jr. et al. | |
| 6,858,026 B2 | 2/2005 | Sliwa, Jr. et al. | |
| 6,869,431 B2 | 3/2005 | Maguire et al. | |
| 6,872,205 B2 | 3/2005 | Lesh et al. | |
| 6,889,694 B2 | 5/2005 | Hooven | |
| 6,893,438 B2 | 5/2005 | Hall et al. | |
| 6,896,673 B2 | 5/2005 | Hooven | |
| 6,899,710 B2 | 5/2005 | Hooven | |
| 6,899,711 B2 | 5/2005 | Stewart et al. | |
| 6,904,303 B2 | 6/2005 | Phan et al. | |
| 6,905,494 B2 | 6/2005 | Yon et al. | |
| 6,905,498 B2 | 6/2005 | Hooven | |
| 6,905,509 B2 | 6/2005 | Dobak, III et al. | |
| 6,908,464 B2 | 6/2005 | Jenkins et al. | |
| 6,920,883 B2 | 7/2005 | Bessette et al. | |
| 6,923,806 B2 | 8/2005 | Hooven et al. | |
| 6,923,808 B2 | 8/2005 | Taimisto | |
| 6,929,639 B2 | 8/2005 | Lafontaine | |
| 6,932,811 B2 | 8/2005 | Hooven et al. | |
| 6,949,095 B2 | 9/2005 | Vaska et al. | |
| 6,949,097 B2 | 9/2005 | Stewart et al. | |
| 6,953,460 B2 | 10/2005 | Maguire et al. | |
| 6,954,977 B2 | 10/2005 | Maguire et al. | |
| 6,955,173 B2 | 10/2005 | Lesh | |
| 6,964,660 B2 | 11/2005 | Maguire et al. | |
| 6,966,908 B2 | 11/2005 | Maguire et al. | |
| 6,971,394 B2 | 12/2005 | Sliwa, Jr. et al. | |
| 6,974,454 B2 | 12/2005 | Hooven | |
| 6,984,233 B2 | 1/2006 | Hooven | |
| 6,997,925 B2 | 2/2006 | Maguire et al. | |
| 7,001,378 B2 | 2/2006 | Yon et al. | |
| 7,001,415 B2 | 2/2006 | Hooven | |
| 7,008,418 B2 * | 3/2006 | Hall et al. | 606/41 |
| 7,044,135 B2 | 5/2006 | Lesh | |
| 7,063,682 B1 | 6/2006 | Whayne et al. | |

(56) References Cited

U.S. PATENT DOCUMENTS

| | | | |
|---|---|---|---|
| 7,142,905 | B2 | 11/2006 | Slayton et al. |
| 7,275,450 | B2 | 10/2007 | Hirai et al. |
| 7,285,116 | B2 | 10/2007 | de la Rama et al. |
| 7,306,593 | B2 | 12/2007 | Keidar et al. |
| 7,393,325 | B2 | 7/2008 | Barthe et al. |
| 2002/0087151 | A1 | 7/2002 | Mody et al. |
| 2003/0050630 | A1 | 3/2003 | Mody et al. |
| 2003/0050631 | A1 | 3/2003 | Mody et al. |
| 2005/0049582 | A1 | 3/2005 | DeBenedictis et al. |
| 2005/0165388 | A1 | 7/2005 | Bhola |
| 2006/0122508 | A1 | 6/2006 | Slayton et al. |
| 2007/0027445 | A1 | 2/2007 | Gifford et al. |
| 2007/0265609 | A1 | 11/2007 | Thapliyal et al. |
| 2007/0265610 | A1 | 11/2007 | Thapliyal et al. |
| 2008/0039746 | A1 | 2/2008 | Hissong et al. |
| 2008/0077200 | A1 | 3/2008 | Bendett et al. |

OTHER PUBLICATIONS

Bushberg et al., *The Essential Physics of Medical Imaging*, 2nd edition, Lippincott Williams & Wilkins 2002, p. 491.

Cox et al. "Current status of the Maze procedure for the treatment of atrial fibrillation," Semin Thorac Cardiovasc Surg. Jan. 2000;12(1):15-9.

Cox et al., "Electrophysiologic basis, surgical development, and clinical results of the maze procedure for atrial flutter and atrial fibrillation," Adv Card Surg. 1995;6:1-67.

Cox et al., "Modification of the maze procedure for atrial flutter and atrial fibrillation. II, Surgical technique of the maze III procedure," J Thorac Cardiovasc Surg. Aug. 1995;110(2):485-95.

Cox et al., "The development of the Maze procedure for the treatment of atrial fibrillation," Semin Thorac Cardiovasc Surg. Jan. 2000;12(1):2-14.

Gentry et al., "Integrated Catheter for 3-D Intracardiac Echocardiography and Ultrasound Ablation," IEEE Transactions on Ultrasonics, Ferroelectrics, and Frequency Control, vol. 51, No. 7, pp. 799-807.

Gill, "How to perform pulmonary vein isolation," Europace, 2004; 6 (2): 83-91; retrieved from the Internet: <<http://europace.oxfordjournals.org/cgi/reprint/6/2/83>>.

Gillinov et al., Atrial fibrillation: current surgical options and their assessment,: Annals of Thoracic Surgery 2002; 74:2210-7; retrieved from the Internet: <<http://ats.ctsnetjournals.org/cgi/reprint/74/6/2210>>.

Haissaguerre et al., "Spontaneous Initiation of Atrial Fibrillation by Ectopic Beats Originating in the Pulmonary Veins," New England J Med., Sep. 3, 1998; 339(10):659-666; retrieved from the Internet: <<http://content.nejm.org/cgi/reprint/339/10/659.pdf>>.

Levinson, "Endocardial Microwave Ablation: A New Surgical Approach for Atrial Fibrillation"; The Heart Surgery Forum, 2006.

Maessen et al., "Beating heart surgical treatment of atrial fibrillation with microwave ablation," Ann Thorac Surg 2002;74:S1307-S1311; retrieved from the Internet: <<http://ats.ctsnetjournals.org/cgi/reprint/74/4/S1307>>.

Nathan et al., "The junction between the left atrium and the pulmonary veins, An anatomic study of human hearts," Circulation 1966; 34:412-422; retrieved from the Internet: <<http://circ.ahajournals.org/cgi/reprint/34/3/412>>.

Sueda et al., "Efficacy of a simple left atrial procedure for chronic atrial fibrillation in mitral valve operations," Ann Thorac Surg 1997; 63:1070-1075.

Sueda et al., "Simple left atrial procedure for chronic atrial fibrillation associated with mitral valve disease," Ann Thorac Surg 1996; 62: 1796-1800.

Ter Haar, "Acoustic Surgery", Physics Today, 2001; 54(12):29-34.

U.S. Appl. No. 12/480,256, filed Jun. 8, 2009; first named inventor: Hira V. Thapliyal.

U.S. Appl. No. 12/483,174, filed Jun. 11, 2009; first named inventor: Hira V. Thapliyal.

U.S. Appl. No. 12/482,640, filed Jun. 11, 2009; first named inventor: Hira V. Thapliyal.

\* cited by examiner

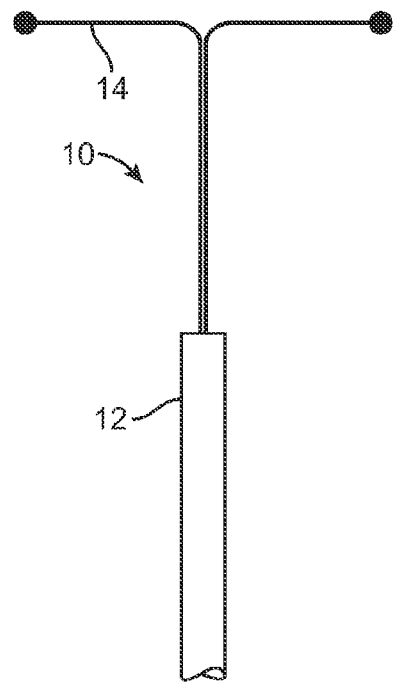
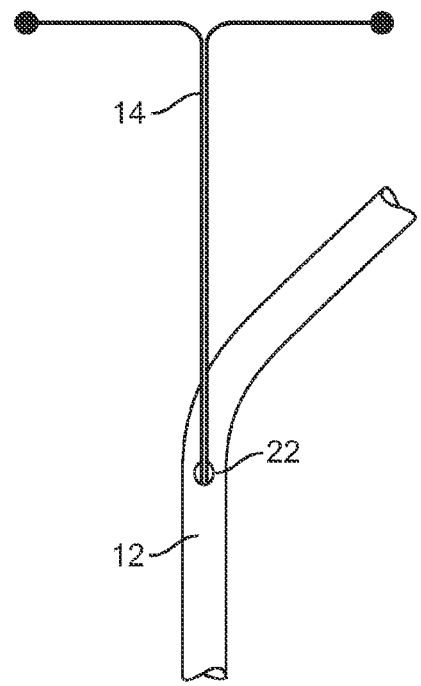
FIG. 1A   FIG. 1B
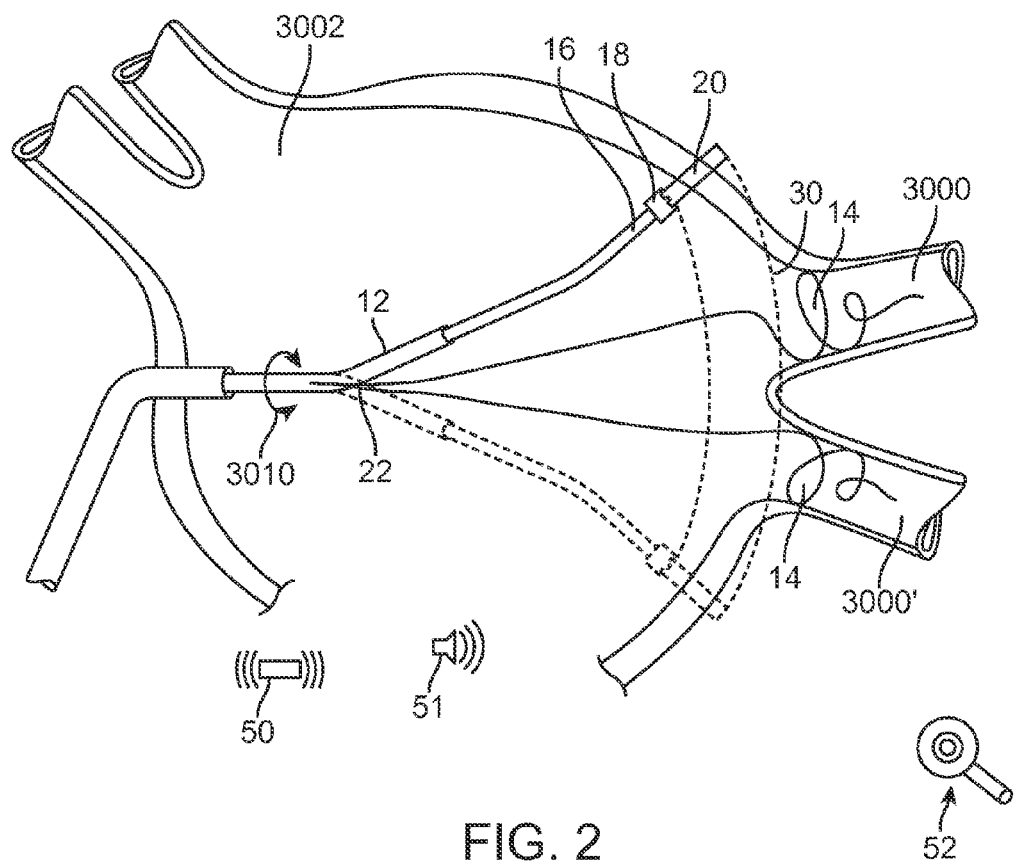
FIG. 2

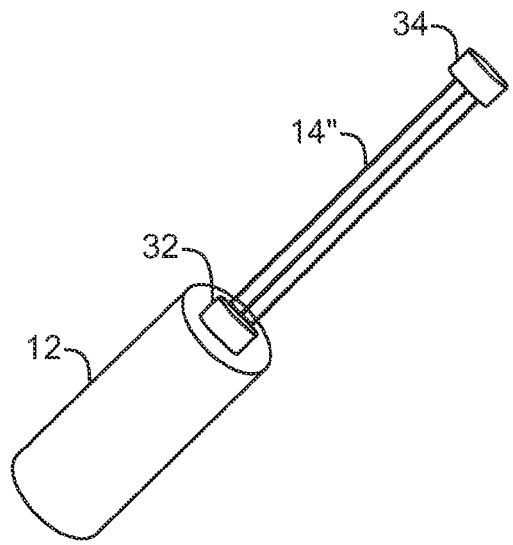
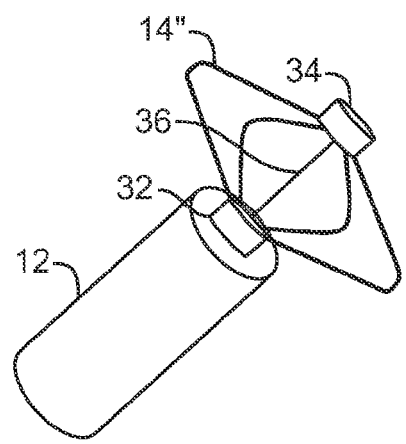
FIG. 9A
FIG. 9B
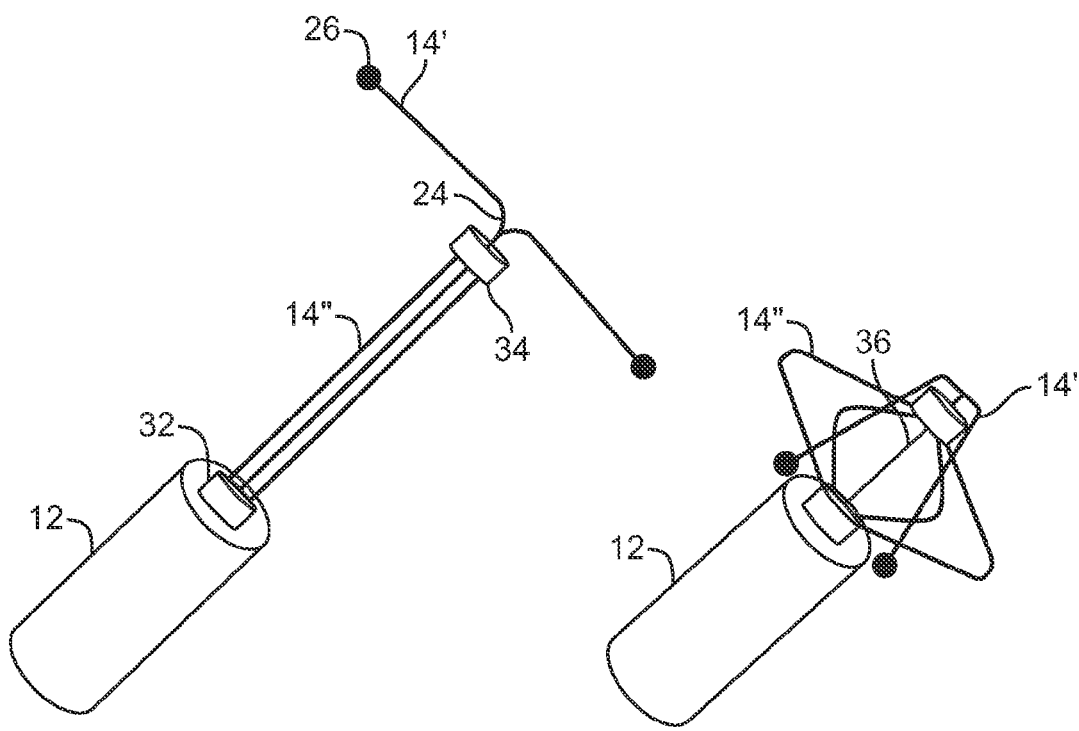
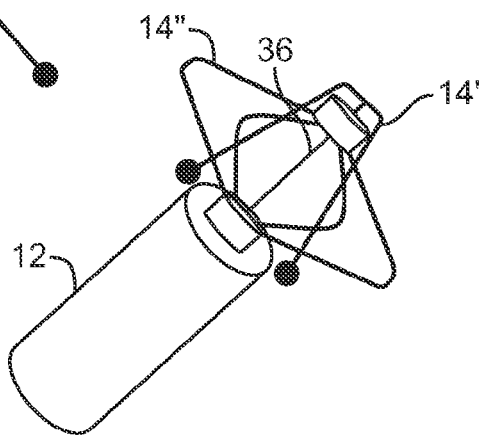
FIG. 10A
FIG. 10B

SYSTEM AND METHOD FOR POSITIONING AN ELONGATE MEMBER WITH RESPECT TO AN ANATOMICAL STRUCTURE

CROSS-REFERENCES TO RELATED APPLICATIONS

This application is a non-provisional of, and claims the benefit of priority under 35 U.S.C. §119(e) of U.S. Provisional Application No. 61/061,362 filed Jun. 13, 2008, the entire contents of which are incorporated herein by reference.

BACKGROUND OF THE INVENTION

1. Field of the Invention

The present invention relates generally to medical devices and methods, and more specifically to improved devices and methods for positioning an ablation device in a human or animal patient. The device may be used to treat atrial fibrillation.

The condition of atrial fibrillation is characterized by the abnormal (usually very rapid) beating of left atrium of the heart which is out of synch with the normal synchronous movement ("normal sinus rhythm") of the heart muscle. In normal sinus rhythm, the electrical impulses originate in the sino-atrial node ("SA node") which resides in the right atrium. The abnormal beating of the atrial heart muscle is known as fibrillation and is caused by electrical impulses originating instead in the pulmonary veins ("PV") [Haissaguerre, M. et al., Spontaneous Initiation of Atrial Fibrillation by Ectopic Beats Originating in the Pulmonary Veins, New England J Med., Vol. 339: 659-666].

There are pharmacological treatments for this condition with varying degrees of success. In addition, there are surgical interventions aimed at removing the aberrant electrical pathways from PV to the left atrium ("LA") such as the Cox-Maze III Procedure [J. L. Cox et al., The development of the Maze procedure for the treatment of atrial fibrillation, Seminars in Thoracic & Cardiovascular Surgery, 2000; 12: 2-14; J. L. Cox et al., Electrophysiologic basis, surgical development, and clinical results of the maze procedure for atrial flutter and atrial fibrillation, Advances in Cardiac Surgery, 1995; 6: 1-67; and J. L. Cox et al., Modification of the maze procedure for atrial flutter and atrial fibrillation. II, Surgical technique of the maze III procedure, Journal of Thoracic & Cardiovascular Surgery, 1995; 2110: 485-95]. This procedure is shown to be 99% effective [J. L. Cox, N. Ad, T. Palazzo, et al. Current status of the Maze procedure for the treatment of atrial fibrillation, Seminars in Thoracic & Cardiovascular Surgery, 2000; 12: 15-19] but requires special surgical skills and is time consuming.

There has been considerable effort to copy the Cox-Maze procedure for a less invasive percutaneous catheter-based approach. Less invasive treatments have been developed which involve use of some form of energy to ablate (or kill) the tissue surrounding the aberrant focal point where the abnormal signals originate in PV. The most common methodology is the use of radio-frequency ("RF") electrical energy to heat the muscle tissue and thereby ablate it. The aberrant electrical impulses are then prevented from traveling from PV to the atrium (achieving conduction block within the heart tissue) and thus avoiding the fibrillation of the atrial muscle. Other energy sources, such as microwave, laser, and ultrasound have been utilized to achieve the conduction block. In addition, techniques such as cryoablation, administration of ethanol, and the like have also been used.

There has been considerable effort in developing the catheter based systems for the treatment of AF using radiofrequency (RF) energy. One such method is described in U.S. Pat. No. 6,064,902 to Haissaguerre et al. In this approach, a catheter is made of distal and proximal electrodes at the tip. The catheter can be bent in a J shape and positioned inside a pulmonary vein. The tissue of the inner wall of the PV is ablated in an attempt to kill the source of the aberrant heart activity. Other RF based catheters are described in U.S. Pat. No. 6,814,733 to Schwartz et al., U.S. Pat. No. 6,996,908 to Maguire et al., U.S. Pat. No. 6,955,173 to Lesh; and U.S. Pat. No. 6,949,097 to Stewart et al.

Another source used in ablation is microwave energy. One such device is described by Dr. Mark Levinson [(Endocardial Microwave Ablation: A New Surgical Approach for Atrial Fibrillation; The Heart Surgery Forum, 2006] and Maessen et al. [Beating heart surgical treatment of atrial fibrillation with microwave ablation. Ann Thorac Surg 74: 1160-8, 2002]. This intraoperative device consists of a probe with a malleable antenna which has the ability to ablate the atrial tissue. Other microwave based catheters are described in U.S. Pat. No. 4,641,649 to Walinsky; U.S. Pat. No. 5,246,438 to Langberg; U.S. Pat. No. 5,405,346 to Grundy, et al.; and U.S. Pat. No. 5,314,466 to Stem, et al.

Another catheter based method utilizes the cryogenic technique where the tissue of the atrium is frozen below a temperature of −60 degrees C. This results in killing of the tissue in the vicinity of the PV thereby eliminating the pathway for the aberrant signals causing the AF [A. M. Gillinov, E. H. Blackstone and P. M. McCarthy, Atrial fibrillation: current surgical options and their assessment, Annals of Thoracic Surgery 2002; 74:2210-7]. Cryo-based techniques have been a part of the partial Maze procedures [Sueda T., Nagata H., Orihashi K., et al., Efficacy of a simple left atrial procedure for chronic atrial fibrillation in mitral valve operations, Ann Thorac Surg 1997; 63: 1070-1075; and Sueda T., Nagata H., Shikata H., et al.; Simple left atrial procedure for chronic atrial fibrillation associated with mitral valve disease, Ann Thorac Surg 1996; 62: 1796-1800]. More recently, Dr. Cox and his group [Nathan H., Eliakim M., The junction between the left atrium and the pulmonary veins, An anatomic study of human hearts, Circulation 1966; 34: 412-422, and Cox J. L., Schuessler R. B., Boineau J. P., The development of the Maze procedure for the treatment of atrial fibrillation, Semin Thorac Cardiovasc Surg 2000; 12: 2-14] have used cryoprobes (cryo-Maze) to duplicate the essentials of the Cox-Maze III procedure. Other cryo-based devices are described in U.S. Pat. Nos. 6,929,639 and 6,666,858 to Lafintaine and U.S. Pat. No. 6,161,543 to Cox et al.

More recent approaches for the AF treatment involve the use of ultrasound energy. The target tissue of the region surrounding the pulmonary vein is heated with ultrasound energy emitted by one or more ultrasound transducers. One such approach is described by Lesh et al. in U.S. Pat. No. 6,502,576. Here the catheter distal tip portion is equipped with a balloon which contains an ultrasound element. The balloon serves as an anchoring means to secure the tip of the catheter in the pulmonary vein. The balloon portion of the catheter is positioned in the selected pulmonary vein and the balloon is inflated with a fluid which is transparent to ultrasound energy. The transducer emits the ultrasound energy which travels to the target tissue in or near the pulmonary vein and ablates it. The intended therapy is to destroy the electrical conduction path around a pulmonary vein and thereby restore the normal sinus rhythm. The therapy involves the creation of a multiplicity of lesions around individual pulmonary veins as required. The inventors describe various configurations for the energy emitter and the anchoring mechanisms.

Yet another catheter device using ultrasound energy is described by Gentry et al. [Integrated Catheter for 3-D Intracardiac Echocardiography and Ultrasound Ablation, IEEE Transactions on Ultrasonics, Ferroelectrics, and Frequency Control, Vol. 51, No.7, pp 799-807]. Here the catheter tip is made of an array of ultrasound elements in a grid pattern for the purpose of creating a three dimensional image of the target tissue. An ablating ultrasound transducer is provided which is in the shape of a ring which encircles the imaging grid. The ablating transducer emits a ring of ultrasound energy at 10 MHz frequency. In a separate publication [Medical Device Link, Medical Device and Diagnostic Industry, February 2006], in the description of the device, the authors assert that the pulmonary veins can be imaged.

While these devices and methods are promising, improved devices and methods for positioning a device relative to an anatomic structure such as the pulmonary vein are needed. Furthermore, it would also be desirable if such devices could create single or multiple ablation zones to block abnormal electrical activity in the heart in order to lessen or prevent atrial fibrillation. Such devices and methods should be easy to use, cost effective and simple to manufacture.

2. Description of Background Art

Other devices based on ultrasound energy to create circumferential lesions are described in U.S. Pat. Nos. 6,997,925; 6,966,908; 6,964,660; 6,954,977; 6,953,460; 6,652,515; 6,547,788; and 6,514,249 to Maguire et al.; U.S. Pat. Nos. 6,955,173; 6,052,576; 6,305,378; 6,164,283; and 6,012,457 to Lesh; U.S. Pat. No. 6,872,205; 6,416,511; 6,254,599; 6,245,064; and 6,024,740; to Lesh et al.; U.S. Pat. No. 6,383,151; 6,117,101; and WO 99/02096 to Diederich et al.; U.S. Pat. No. 6,635,054 to Fjield et al.; U.S. Pat. No. 6,780,183 to Jimenez et al.; U.S. Pat. No. 6,605,084 to Acker et al.; U.S. Pat. No. 5,295,484 to Marcus et al.; and WO 2005/117734 to Wong et al.

In all above approaches, the inventions involve the ablation of tissue inside a pulmonary vein or at the location of the ostium. The anchoring mechanisms engage the inside lumen of the target pulmonary vein. In all these approaches, the anchor is placed inside one vein, and the ablation is done one vein at a time.

BRIEF SUMMARY OF THE INVENTION

The present invention generally relates to medical devices and methods and more particularly relates to devices and methods for positioning an ablation device used in the treatment of atrial fibrillation.

In a first aspect of the present invention, an ablation device for treating atrial fibrillation in a patient comprises an elongate shaft having a proximal end and a distal end. A positioning mechanism is adjacent the distal end of the shaft and is adapted to facilitate location of an anatomic structure and also adapted to anchor the elongate shaft adjacent the anatomic structure. The positioning mechanism comprises an electrode for stimulating the anatomic structure and also for sensing electrical signals from the anatomic structure. An energy delivery element is adjacent the distal end of the shaft and is adapted to stimulate the anatomic structure and create a zone of ablation that blocks abnormal electrical activity thereby reducing or eliminating atrial fibrillation in the patient.

The elongate shaft may comprise a lumen extending between the proximal and distal ends of the shaft. The shaft may be rotatable around the positioning mechanism. The shaft may also have a sidewall with a window therethrough, and the energy delivery element may be adapted to stimulate the anatomic structure through the window.

The positioning mechanism may be slidably disposed in the lumen, and it may be in a substantially linear configuration while disposed in the lumen. The positioning mechanism may exit the shaft via an aperture in a sidewall of the shaft. The positioning mechanism may comprises a coil or a plurality of wires expandable from a contracted configuration to an expanded configuration. In the expanded configuration, the plurality of wires may form a cage-like structure. The plurality of wires may also be biased to flare radially outward when unconstrained. The positioning mechanism may be adapted to exert an outward biasing force against an interior surface of the anatomical structure thereby anchoring the elongate shaft thereto. The anatomic structure may be a pulmonary vein and the positioning mechanism may be adapted to indicate an angle of entry of the elongate shaft into the pulmonary vein. In still other embodiments, the positioning mechanism may comprise a proximal wire and a distal wire, both proximal and distal wires at least partially encircling the elongate shaft.

The electrode may operate in a monopolar mode or the electrode may comprise a plurality of electrodes operating in a bipolar mode.

The energy delivery element may comprise an ultrasound transducer. The energy delivery element may also be adapted to deliver radiofrequency energy, microwaves, light energy, thermal energy, or cryogenic cooling to the anatomic structure. The zone of ablation may be a linear region, an annular region, or an arcuate. The zone of ablation may encircle one or more than one pulmonary veins or the zone of ablation may be outside of and adjacent a pulmonary vein. The energy delivery element often may remain unobstructed by the positioning mechanism.

In another aspect of the present invention, a method of ablating an anatomic structure in a patient as a treatment for atrial fibrillation comprises providing an elongate shaft having a proximal end and a distal end and locating the anatomic structure with a positioning mechanism disposed adjacent the distal end of the shaft. The shaft is anchored adjacent the anatomic structure with the positioning mechanism and an electrode adjacent a distal portion of the positioning mechanism is used to electrically stimulate or sense electrical signals from the anatomic structure. Energy is delivered to the anatomic structure with an energy delivery element near the distal end of the shaft, thereby creating a zone of ablation that blocks abnormal electrical activity in order to reduce or eliminate atrial fibrillation in the patient.

The elongate shaft may comprise a lumen extending between the proximal and distal ends and the method may further comprise delivering a fluid from the lumen to the anatomic structure. The step of locating the anatomic structure may comprise visualizing the anatomic structure, or tactile or audible feedback. The positioning mechanism may be advanced from or retracted into the elongate shaft during the step of locating. The positioning mechanism may comprise a plurality of wires and the anatomic structure may be located by deflecting at least some of the plurality of wires. Locating the anatomic structure may also comprise determining an entry angle of the elongate shaft into the anatomic structure.

The step of anchoring the shaft may comprise engaging the positioning mechanism against the anatomical structure and exerting an outward biasing force against an interior surface of the anatomical structure. Anchoring may also comprise forming and engaging a cage-like structure on the positioning mechanism with the anatomic structure.

The step of stimulating the anatomic structure may comprise stimulating in a monopolar or bipolar mode. Stimulating may also comprise pacing the patient's heart. The stimulating step may be performed before, during or after creation of the ablation zone.

Delivering energy to the anatomic structure may comprise delivering one of ultrasound energy, radiofrequency energy, microwave, light, and thermal energy. The step of creating the zone of ablation may comprise creating a linear or arcuate ablation path such as when the zone of ablation encircles one or more than one pulmonary vein. Sometimes the elongate shaft may be rotated around the positioning mechanism while delivering energy. The energy may be delivered through a window in the elongate shaft and the energy may be directed at an angle between 65 and 115 degrees to the anatomic structure. Delivering energy may comprise adjusting power, frequency, bandwidth, or amplitude of the energy delivered to the anatomic structure. The method may further comprise cooling the anatomic structure with cooling fluid.

These and other embodiments are described in further detail in the following description related to the appended drawing figures.

BRIEF DESCRIPTION OF THE DRAWINGS

FIGS. 1A and 1B are drawings of the system of the preferred embodiment of the invention;

FIGS. 2-4 are drawings of three rotation variations of the system of the preferred embodiment of the invention;

FIGS. 9A and 9B are drawings of a second variation of the positioning mechanism of the system of the preferred embodiment of the invention;

FIGS. 10A and 10B are drawings of a third variation of the positioning mechanism of the system of the preferred embodiment of the invention;

DETAILED DESCRIPTION OF THE INVENTION

Figure 3:
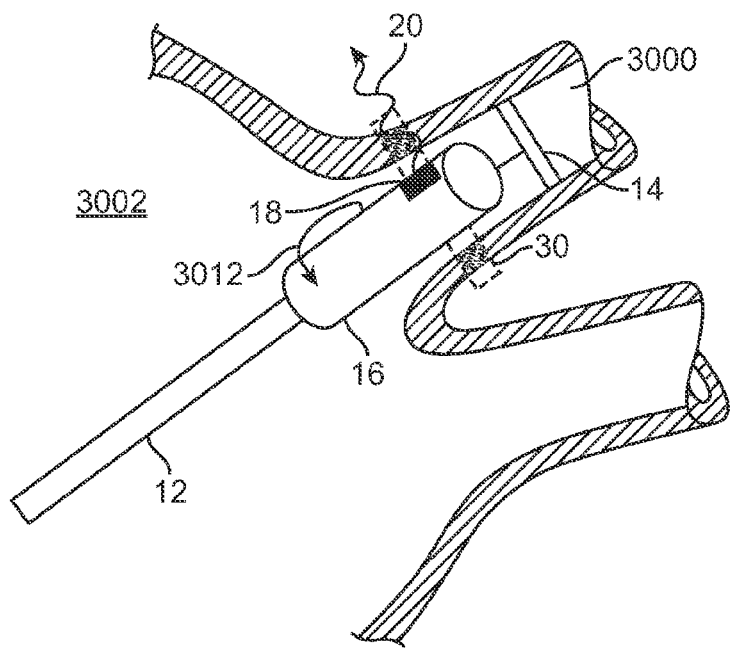

The following description of preferred embodiments of the invention is not intended to limit the invention to these embodiments, but rather to enable any person skilled in the art to make and use this invention.

As shown in FIGS. 1A and 2, the system 10 of the preferred embodiments includes an elongate member 12 and a positioning mechanism 14 coupled to the elongate member 12. The elongate member 12 may be radiopaque to allow it to be seen during fluoroscopy. This may be achieved with radiopaque marker bands or by including radiopaque filler materials in the elongate member such as barium sulfate or titanium dioxide. The positioning mechanism 14 performs one or more of the following functions: (a) facilitate locating an anatomical structure (preferably a pulmonary vein 3000 in a left atrium of a heart 3002, but alternatively any other suitable anatomical structure), (b) anchor the elongate member 12 with respect to the anatomical structure, and (c) electrically stimulate and/or sense electrical signals from the anatomical structure. The system 10 is preferably designed for positioning an elongate member within a patient and, more specifically, for positioning a therapy and/or navigation catheter with respect to a pulmonary vein in the left atrium of the heart of a patient. The system 10, however, may be alternatively used in any suitable environment and for any suitable reason.

The Elongate Member. The elongate member 12 of the preferred embodiments is a catheter made of a flexible multi-lumen tube, but may alternatively be a cannula, tube or any other suitable elongate structure having one or more lumens. The elongate member 12 preferably has a separate lumen that houses the positioning mechanism 14, but may alternatively house the positioning mechanism 14 in any other suitable configuration. The elongate member 12 preferably houses a single positioning mechanisms 14 (as shown in FIG. 1A), but may house more than one positioning mechanisms (as shown in FIG. 2). The elongate member 12 of the preferred embodiments functions to accommodate pull members, fluids, gases, energy delivery structures, electrical connections, therapy catheters, navigation catheters, pacing catheters, and/or any other suitable device or element. As shown in FIG. 2, the elongate member 12 preferably includes a distal tip assembly 16 positioned at a distal portion of the elongate member 12. The distal tip assembly 16 preferably houses an energy delivery structure 18 that functions to deliver energy 20 to tissue, such as tissue of a heart 3002. The energy delivery structure 18 preferably includes an ultrasound transducer subassembly, but may alternatively include any other suitable source of ablation energy such as radio frequency (RF) energy, microwaves, photonic energy, and thermal energy. Ablation could alternatively be achieved using cooled fluids (e.g., cryogenic fluid).

Figure 5:
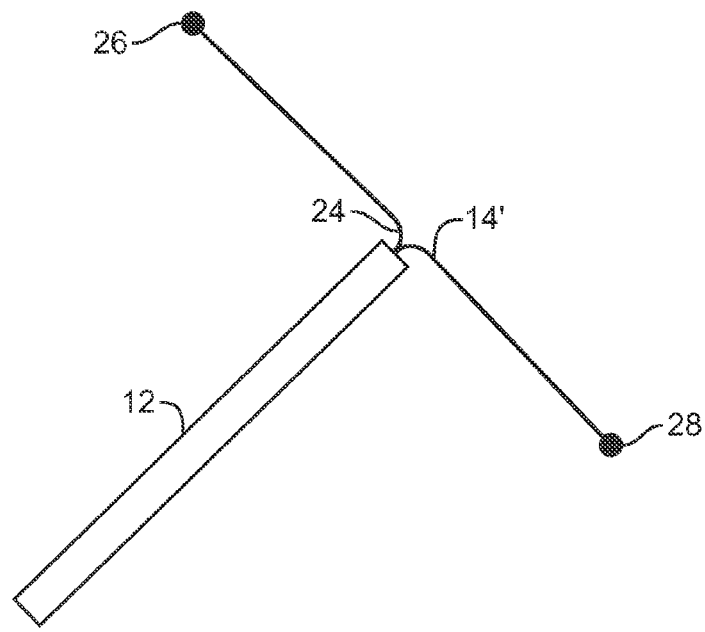
FIGS. 5-8C are drawings of a first variation of the positioning mechanism of the system of the preferred embodiment of the invention.
Figure 11:
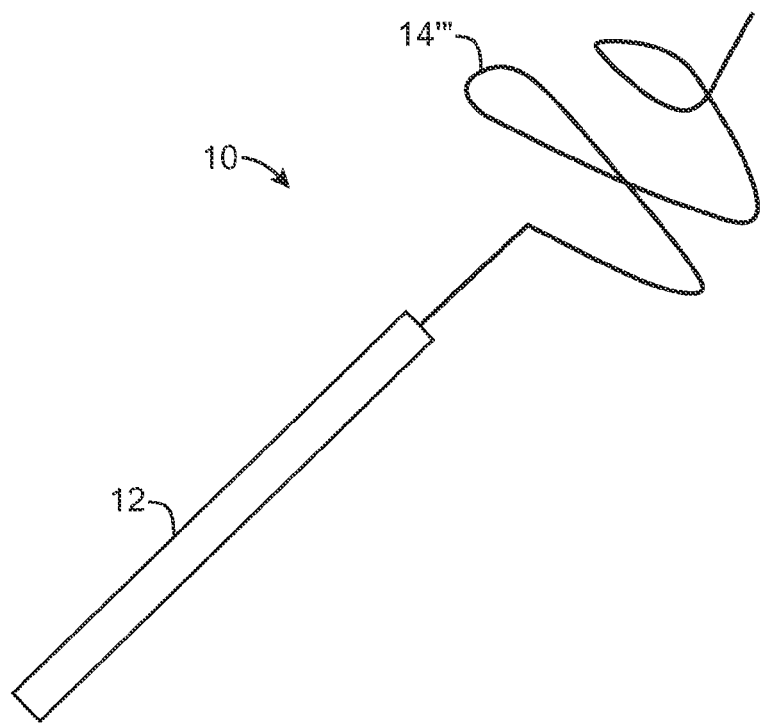
FIG. 11 is a drawing of a fourth variation of the positioning mechanism of the system of the preferred embodiment of the invention.

The Positioning Mechanism. As shown in FIGS. 1A and 1B, the positioning mechanism 14 of the preferred embodiments is coupled to a distal portion of the elongate member 12. As shown in FIG. 1A, the positioning mechanism 14 is preferably coupled to the distal tip of the elongate member 12. The positioning mechanism 14 is preferably coupled to the distal tip of the elongate member 14 such that fluid (for cooling the energy delivery system 18 or for cooling the tissue, for example) is able to flow through a lumen in the elongate member 12 and exit out of the elongate member as necessary. Alternatively, as shown in FIG. 1B, the positioning mechanism 14 is preferably coupled to the side of the elongate member 12 near the distal end of the elongate member 12. In some variations, the positioning member 14 is retractable into and exits from the elongate member 12 through the distal end or through a notch 22 near the distal end of the elongate member 12. In these variations, the positioning member 14 preferably is held in or moves to a smaller configuration (by folding, straightening, etc.) such that it fits within the elongate member 12. The positioning member, when residing completely inside a lumen of the elongate member 12, is preferably held in a generally straight shape, conforming to confines of the lumen. As the positing member 14 is advanced outwards, and/or as it exits the notch 22, it preferably takes on a predetermined shape, for example as shown in FIGS. 1B, 5, and 11.

As shown in FIG. 2, the positioning mechanism 14 of the preferred embodiments performs one or more of the following functions: (a) facilitate locating an anatomical structure, (b) anchor the elongate member 12 with respect to the anatomical structure, and (c) electrically stimulate and/or sense electrical signals from the anatomical structure. Regarding the first function, the positioning mechanism 14 facilitates locating an anatomical structure by providing an indication of where the positioning mechanism 14 is with respect to the anatomical structure. The indication is preferably a visual indication (via a medical imaging system such as a fluoroscope), but is alternatively or additionally a tactile indication 50 or audible indication 51. FIG. 2 also illustrates visualization of the anatomic structure 52. Additionally, the elongate member 12 and/or the positioning mechanism 14 may include indicia, such as markings indicating distance, that indicate the location of the anatomical structure and/or to indicate the depth of insertion of the system 10 where the anatomical structure was located.

Regarding the second function, the positioning mechanism 14 anchors the elongate member 12 with respect to the anatomical structure by coupling to a portion of an anatomical structure (for example a pulmonary vein 3000 and/or a left atrium 3002 of a heart) and by providing stabilization of the elongate member 12 when manipulating at least a portion of the elongate member 12 and/or by providing an axis of rotation to the elongate member 12 as it is rotated. The elongate member 12 is preferably manipulated to position the energy delivery structure 18 within the left atrium of the heart 3002 (or in any other suitable location) and, once positioned there, is preferably manipulated to move the energy delivery structure 18 along an ablation path and to direct the energy delivery structure 18 towards tissue to provide a partial or complete zone of ablation along the ablation path. The ablation path preferably has any suitable geometry or geometries to provide a conduction block—isolation and/or block of conduction pathways of abnormal electrical activity, which typically originate from the pulmonary veins in the left atrium—for treatment of atrial fibrillation in a patient, but may alternatively provide any other suitable therapy. A linear ablation path is preferably created by moving and bending the elongate member 12 in an X, Y, and/or Z direction. A generally circular or elliptical ablation path 30 is preferably created by rotating the elongate member 12 about an axis. The elongate member 12 is preferably rotated in one of several variations. In a first variation, as shown in FIG. 2, the elongate member is rotated, as shown by arrow 3010, around the two positioning mechanisms 14, the energy delivery structure 18 preferably sweeps a generally circular ablation path 30. The two positioning mechanisms 14 preferably assure that the rotation of the elongate member 12 and therefore the energy delivery structure 18 will occur in an ablation path 30 outside of the pulmonary veins 3000 and 3000'. The ablation path 30 may alternatively encircle a single pulmonary vein or encircle any other suitable number of pulmonary veins.

In a second variation, as shown in FIG. 3, the elongate member is rotated, as shown by arrow 3012, within the pulmonary vein 3000 such that the energy delivery structure 18 preferably sweeps a generally circular ablation path 30, generally perpendicular to the axis of the pulmonary vein 3000. In an alternative version of this second variation, the elongate member may alternatively be located outside of and adjacent to the pulmonary vein while still generally perpendicular to the axis of the pulmonary vein 3000. The elongate member is preferably rotated such that the energy delivery structure 18 preferably sweeps a generally circular ablation path 30 around at least one ostium of a pulmonary vein. In this version of the second variation, the energy delivery structure 18 is preferably angled such that it is preferably at an acute angle with respect to the axis of the elongate member and such that the energy delivery structure preferably points and delivers energy 20 substantially towards the atrial wall and around the pulmonary vein ostium. In the second variation, the energy delivery structure 18 preferably rotates within the distal tip assembly 16, delivering ablation energy though a window that runs around the circumference of the distal tip assembly 16. The window is preferably made of a material that is transparent to ultrasound waves such as a poly 4-methyl, 1-pentene (PMP) material or may alternatively be an open window. Alternatively, the elongate member 12 and/or distal tip assembly 16 may rotate, rotating the energy delivery structure within. The positioning mechanism 14 preferably does not rotate along with the elongate member 12 and/or the distal tip assembly 16.

Figure 4:
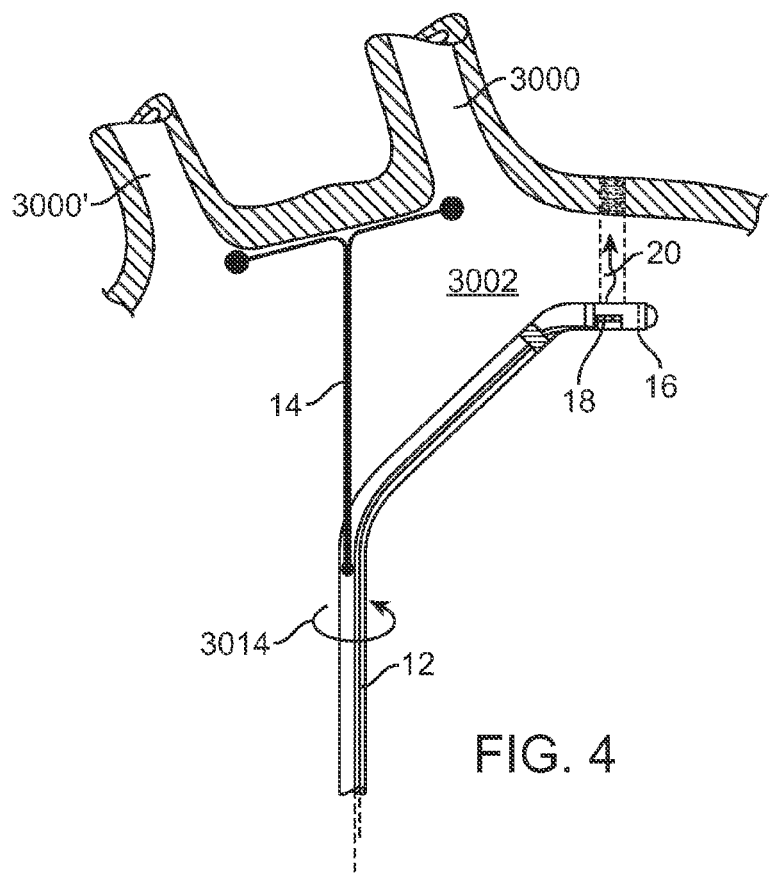

In a third variation, as shown in FIG. 4, the positioning mechanism 14 is pressed against a portion of a heart chamber (such as the ceiling wall of the left atrium), or in any other suitable location and the elongate member 12 is rotated, as shown by arrow 3014, around the axis created by the positioning mechanism 14, the energy delivery structure 18 preferably sweeps a generally circular ablation path outside of the pulmonary veins 3000 and 3000'. The ablation path may alternatively encircle a single pulmonary vein or any other suitable number of pulmonary veins.

In all variations, the energy delivery structure is preferably positioned with respect to the tissue at an appropriate angle. The energy delivery system is preferably directed towards the target tissue at an angle between 20 and 160 degrees to the tissue, more preferably at an angle between 45 and 135 degrees to the tissue, and most preferably at an angle of 65 and 115 degrees to the tissue.

Regarding the third function, the positioning mechanism 14 electrically stimulates and/or senses electrical signals from the anatomical structure by electrically coupling to the anatomical structure and sending and/or receiving electrical signals to the tissue. The positioning mechanism 14 preferably includes an even number of electrodes or electrically active portions such that a bipolar electrical system may be used, wherein each pair of electrodes or electrically active portions has an opposite polarity. The positioning mechanism 14 may alternatively include a single electrode or electrically active portion and use a monopolar electrical system, or may include any other suitable number of electrodes or electrically active portions. The positioning mechanism 14 functions to map the tissue by sensing the electrical conduction between the pulmonary veins and the other parts of the atrial wall on the endocardial side. The positioning mechanism 14 functions to pace the tissue and maintain an artificial heart rate (preferably temporarily) by sending electrical pulses to the tissue. The positioning mechanism 14 preferably paces the tissue located in a position distal from the energy delivery structure 18 and/or the ablation path 30, such that the energy delivery structure 18 and/or the ablation path 30 are between the positioning mechanism 14 that is pacing and the beating heart. The positioning mechanism may alternatively pace tissue in any other suitable location. The recording and sensing signals received and sent by the positioning mechanism are preferably compatible with conventional navigation and mapping systems such as CARTO XP EP Navigation System (Biosense Webster, Diamond Bar, Calif.), EnSite System (St. Jude Medical, St. Paul, Minn.), and/or any other suitable mapping, navigation, or visualization system.

As mentioned above, the positioning mechanism 14 of the preferred embodiments performs one or more of the following functions: (a) facilitate locating an anatomical structure, (b) anchor the elongate member 12 with respect to the anatomical structure, and (c) electrically stimulate and/or sense electrical signals from the anatomical structure. Although the positioning mechanism 14 is preferably one of the several variations described below, the positioning mechanism 14 may be any suitable mechanism to perform one or more of these functions.

Figure 6A:
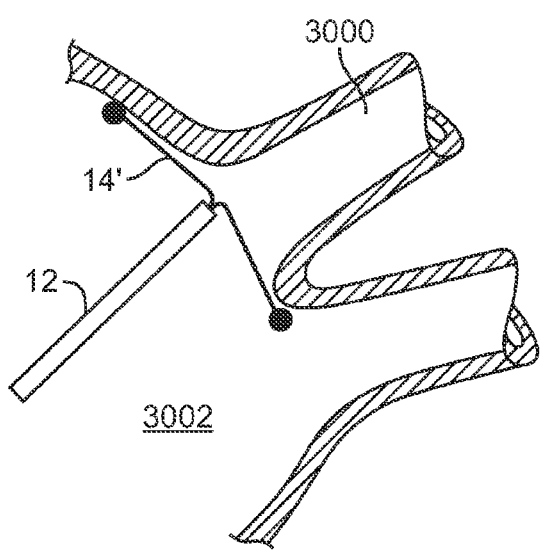
Figure 6B:
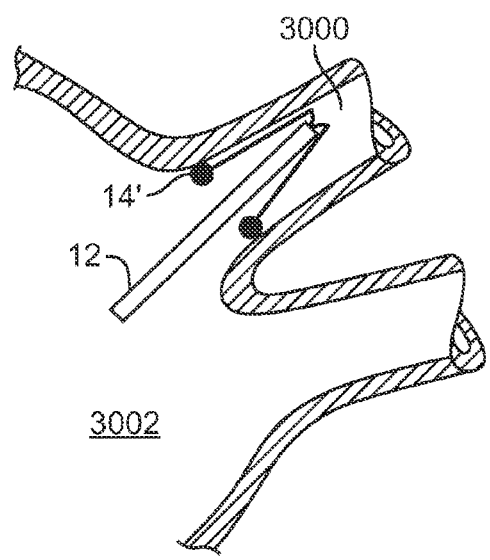

First Variation of the Positioning Mechanism. In a first variation, as shown in FIGS. 5, 6A, and 6B, the positioning mechanism 14' includes a plurality of wires each having a first end 24 and a second end 26. The plurality of wires are preferably flexible wires, but may alternatively be movable in any other suitable fashion. The first end 24 is preferably coupled to the distal tip of the elongate member 12, but may alternatively be attached in any other suitable location (shown in FIG. 4). The second end 26 preferably extends from the distal tip of the elongate member and is positioned in a fully extended position, as shown in FIG. 5. The second end 26 preferably deflects due to contact with a surface, as shown in FIGS. 6A and 6B. The second end 26 is preferably biased towards the fully extended position, but may alternatively be biased towards any other suitable position. The first end 24 is preferably slidably coupled to the elongate member 12 such that it is partially or fully retractable into the elongate member 12. For example, the plurality of wires may be pushed or pulled through the distal tip of the elongate member 12 by a wire that extends through the elongate member 12. The plurality of wires may be pulled back through the distal tip of the elongate member 12 in order to return the wires to the fully extended position, as shown in FIG. 5. The plurality of wires may alternatively be fixed to the distal tip of the elongate member 12 or coupled to the elongate member 12 in any other suitable fashion. The wires are preferably made from a conductive material and/or a material with shape memory such as nickel/titanium or a shape memory polymer. The material is preferably flexible so as not to cause injury to the tissue of the heart where the positioning mechanism 14' might contact and move against it. At least a portion of each wire is preferably made from a fluoro-opaque material, such as platinum or gold, such that it may be seen while positioned inside the internal structures of a patient through the use of a fluoroscope. The fluoro-opaque portion 28 is preferably located at the second end 26 of a wire, but may alternatively be located in any suitable position such that it may be seen while positioned inside the internal structures of a patient through the use of a fluoroscope. The fluoro-opaque portion is preferably flush with the wire, but may alternatively have a round or any other suitable shape such that it will not damage the tissue. Additionally, the plurality of wires preferably includes at least one electrically active portion and/or at least one insulated portion (e.g. an insulating coating on a portion of each wire). The electrically active portion is preferably located at the second end 26 of a wire, but may alternatively be located in any suitable position, such as the center portion, such that it conies in contact with tissue.

Figure 8A:
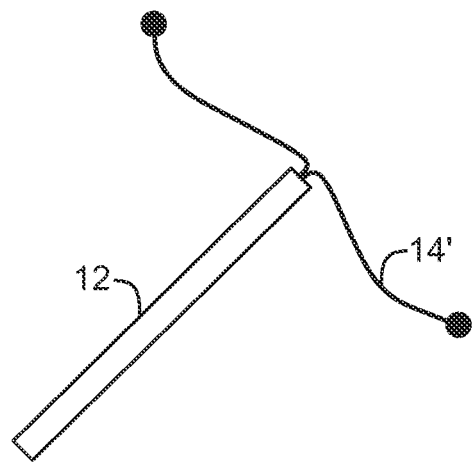
Figure 8B:
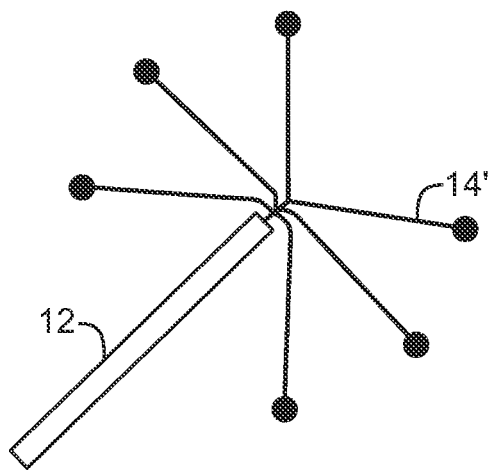
Figure 8C:
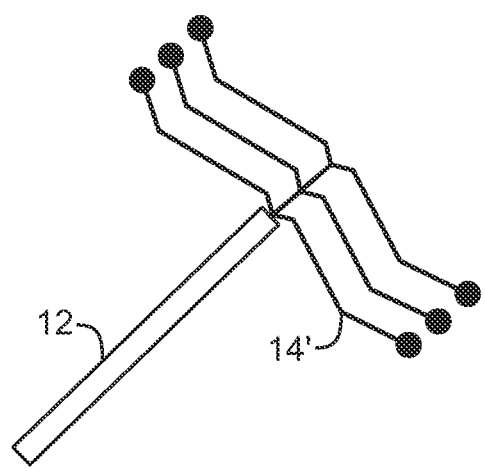

The plurality of wires preferably has any suitable geometry such that positioning mechanism 14' may perform any combination of functions described. Additionally, the plurality of wires preferably have a length and/or geometry such that when they deflect, they do not cover, block, or lay in front of the energy delivery structure 18, or any portion thereof. Therefore, they preferably do not block any portion of the energy delivered by the energy delivery structure 18 and cause a "shadow" effect. In a first version, as shown in FIG. 5, the wires are substantially straight. In a second version, as shown in FIG. 8A, the wires are curved or bent such that they are biased away from the elongate member 12. In a third version, as shown in FIG. 8B, the plurality of wires includes six wires circumferentially disposed around the elongate member 12. The plurality of wires preferably includes an even number of wires, but may alternatively include a single wire or any other suitable number of wires. In a fourth version, as shown in FIG. 8C, the plurality of wires includes multiple tiers or layers of wires. Each tier or layer may include any suitable number of wires and each tier or level may include a different number of wires from any other tier or level.

As shown in FIGS. 6A and 6B, the plurality of wires function to facilitate locating an anatomical structure by flexing as they come in contact with the anatomical structure. For example, the wires will remain fully extended from the elongate member 12 when they are unobstructed in the left atrium of the heart 3002, as shown in FIG. 4. As the system 10 is moved within the left atrium of the heart 3002 and begins to contact the ostium (opening) of a pulmonary vein 3000, the plurality of wires will begin to deflect partially, as shown in FIG. 6A. As the system 10 is moved into the pulmonary vein 3000, the wires will deflect more dramatically as shown in FIG. 6B. As the system is moved deeper into the pulmonary vein, the wires will not deflect as much, if at all, and an operator of the system 10 will be able to determine when the positioning mechanism 14 of the system 10 is correctly located within the pulmonary vein.

Figure 7:
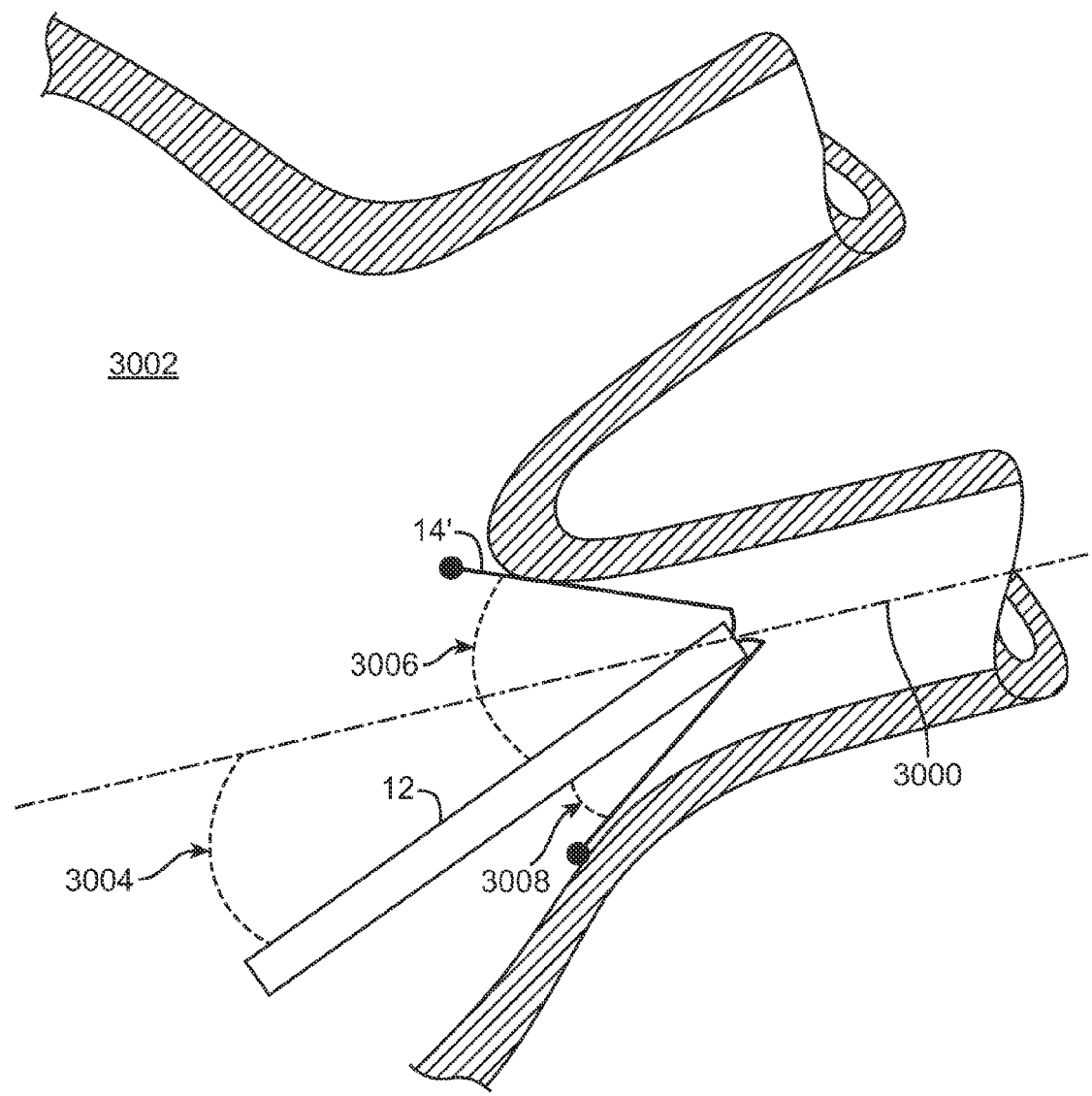

Furthermore, as shown in FIG. 7, the angle 3004 at which the system 10 enters the pulmonary vein 3000 with respect to the longitudinal axis of the pulmonary vein 3000 is determined. For example, if the system 10 is entering the pulmonary vein 3000 at angle 3004, a wire to the left of the elongate member 12 will deflect to an angle 3006 with respect to the elongate member 12 while a wire to the right of the elongate member 12 will deflect to an angle 3008 with respect to the elongate member 12. Therefore, the angle 3004 at which the system 10 is entering the pulmonary vein 3000 is preferably determined from the size of angles 3006 and 3008. These angles 3006 and 3008 are preferably detected visually under fluoroscopic guidance by the operator of the system 10, but may alternatively be detected and processed by a processor in order to determine angle 3004. Upon the detection of the angle 3004, an operator of the system 10 is alerted of an off-center entry, the operator adjusts and centers the system 10 and/or is instructed on how to do so. The system 10 may alternatively be adjusted automatically through a motor drive system or any other suitable system. The ablation path 30 is preferably altered such that energy delivery structure will be located substantially the same distance from each point of tissue along the ablation path 3 and/or the energy delivery structure is preferably adjusted to accommodate an off-center entry. The energy delivery structure is preferably adjusted by changing the power and/or frequency, bandwidth, and amplitude of the sound wave propagated into the tissue along certain portions of an ablation path 30. Due to an off-center entry, the energy delivery structure will be closer to some tissue along the ablation path 30 and further away from other tissue. In one example, the energy delivery structure is adjusted to use less power for the portions of the tissue that are closer to the energy delivery structure.

The plurality of wires function to anchor the elongate member 12 with respect to the anatomical structure, preferably a pulmonary vein 3000, by coupling to the anatomical structure. The outward biasing force of the plurality of wires against the interior wall of the pulmonary vein will preferably hold the positioning mechanism 14' within the pulmonary vein due to friction. Alternatively, the tips of the plurality of wires may function as barbs such that the plurality of wires are preferably advanced into the pulmonary vein, but the tips of the wires will prevent the positioning mechanism 14 from being pulled out of the pulmonary vein. In this version, the wires may be manually retracted upon completion of the procedure to allow for the removal of the positioning mechanism 14'. The positioning mechanism may alternatively function to anchor the elongate member 12 with respect to the anatomical structure in any other suitable fashion.

Second Variation of the Positioning Mechanism. In a second variation, as shown in FIGS. 9A and 9B, the positioning mechanism 14" includes a plurality of wires, a first end cap 32, a second end cap 34, and a pull member 36. The plurality of wires are circumferentially disposed around the elongate member 12. The plurality of wires preferably includes an even number of wires such as two, four, six, eight, or more, but may alternatively include a single wire or any other suitable number of wires. The first end cap 32 is preferably coupled to the distal tip of the elongate member 12, but may alternatively be attached in any other suitable location, as shown in FIG. 4. The second end cap 34 preferably extends from the distal tip of the elongate member 12 along the longitudinal axis of the elongate member 12 and transitions between a fully extended position, as shown in FIG. 9A, and a retracted position, as shown in FIG. 9B. When the second end cap 34 is in the fully extended position, the wires are preferably substantially straight. When the second end cap 34 is in the retracted position, the wires preferably flex and bend at one location along the wire to form a basket or cage-like structure. The second end cap 34 preferably transitions between a fully extended position and a retracted position by pulling the pull member 36. The pull member 36 is preferably coupled to the second end cap 34 and runs through the first end cap 32 such that the first end cap 32 is slidably coupled to the pull member 36. Preferably, the pull member 36 is attached to the second end cap 34 with an adhesive band, but may alternatively be coupled to the second end cap 34 with any other suitable chemical and/or mechanical connection such as adhesive, welding, pins and/or screws. The pull member is preferably disposed within a lumen of the first end cap and the elongate member 12, but may alternatively be held in any suitable location. The pull member preferably terminates at a slider in a proximal housing (not shown) that preferably includes various actuating mechanisms to transition the second end cap from the fully extended position to the retracted position. The second end cap preferably returns to the fully extended position by the spring force of the plurality of wires (they are preferably biased towards the substantially straight position), but may alternatively return to the fully extended position in any other suitable fashion.

The wires may alternatively flex or bend in multiple locations and each wire may bend in a different location. The wires are preferably biased towards the substantially straight position, but may alternatively be biased towards the bent position or any other suitable position. The wires are preferably made from a conductive material and/or a material with shape memory such as nickel/titanium alloys or a shape memory polymer, but may alternatively be made from any suitable material such as plastic. The material is preferably flexible so as not to cause injury to the tissue of the heart where the positioning mechanism 14 might contact and move against it. At least a portion of each wire is preferably made from a fluoro-opaque material (also referred to herein using the term "radiopaque"), such as platinum or gold, such that it may be seen while positioned inside the internal structures of a patient through the use of a fluoroscope. The fluoro-opaque portion is preferably located in any suitable position such that it may be seen while positioned inside the internal structures of a patient through the use of a fluoroscope. The fluoro-opaque portion is preferably flush with the wire, but may alternatively have a round or any other suitable shape such that it will not damage the tissue. Additionally, the plurality of wires preferably includes at least one electrically active portion and/or at least one insulated portion (e.g. an insulating coating on a portion of each wire). The electrically active portion is preferably located towards the center portion of each wire, but may alternatively be located in any suitable position such that it comes in contact with tissue.

The positioning mechanism 14" functions to facilitate locating an anatomical structure by the plurality of wires flexing as they come in contact with the anatomical structure. For example, when the wires are flexed or bent as shown in FIG. 9B, and as the system 10 is moved within the left atrium of the heart 3002 and begins to contact the ostium (opening) of a pulmonary vein 3000, the plurality of wires will begin to deflect inward or away from the adjacent wires due to contact with a tissue surface. As the system is moved deeper into the pulmonary vein, the wires will not deflect as much if at all, and an operator of the system 10 will be able to determine when the positioning mechanism 14" of the system 10 is correctly located within the pulmonary vein.

The plurality of wires of the positioning mechanism 14" function to anchor the elongate member 12 with respect to the anatomical structure, preferably a pulmonary vein 3000, by coupling to the anatomical structure. Preferably, the outward force of the plurality of wires in the flexed or bent position, as shown in FIG. 9B, against the interior wall of the pulmonary vein will hold the positioning mechanism 14" within the pulmonary vein due to friction. In this version, the second end cap 34 will be returned to the fully extended position upon completion of the procedure, straightening the plurality of wires, to allow for the removal of the positioning mechanism 14". The positioning mechanism 14" may alternatively function to anchor the elongate member 12 with respect to the anatomical structure in any other suitable fashion.

Third, Fourth, and Fifth Variation Positioning Mechanism. In a third variation, as shown in FIGS. 10A and 10B, the positioning mechanism is a combination of the first and second variations of the positioning mechanisms 14' and 14". In this variation, the positioning mechanism preferably includes two pluralities of wires. The first plurality of wires has a first end 24 and a second end 26 as described above, and the second plurality of wires has a first end cap 32, a second end cap 34, and a pull member 36 also as described above. When the second end cap 34 is in the retracted position, as shown in FIG. 10B, the second plurality of wires preferably flex and bend in one location to form a basket or cage-like structure. The first plurality of wires deflect due to contact with a surface and will preferably deflect down and in between the second plurality of wires such that they will not obstruct the function of the second plurality of wires.

In a fourth variation, as shown in FIG. 11, the positioning mechanism 14''' is a coil. The coil is preferably made from a conductive material and/or a material with shape memory such as nickel/titanium alloys or a shape memory polymer. The material is preferably flexible so as not to cause injury to the tissue of the heart where the positioning mechanism 14 might contact and move against it. At least a portion of the coil is preferably made from a fluoro-opaque material, such as platinum or gold, such that it may be seen while positioned inside the internal structures of a patient through the use of a fluoroscope. The fluoro-opaque portion is preferably located in any suitable position such that it may be seen while positioned inside the internal structures of a patient through the use of a fluoroscope. The fluoro-opaque portion is preferably flush with the wire, but may alternatively have a round or any other suitable shape such that it will not damage the tissue. Additionally, the coil preferably includes at least one electrically active portion and/or at least one insulated portion (e.g. an insulating coating on a portion of each wire). The electrically active portion is preferably located in any suitable position such that it comes in contact with tissue.

The positioning mechanism 14''' functions to facilitate locating an anatomical structure by the coil flexing as it comes in contact with the anatomical structure. For example, as the system 10 is moved within the left atrium of the heart 3002 and begins to contact the wall of the atrium or the ostium (opening) of a pulmonary vein 3000, the coil will begin to deflect. As the system is moved deeper into the pulmonary vein, the wires will not deflect as much if at all, and an operator of the system 10 will be able to determine when the positioning mechanism 14''' of the system 10 is correctly located within the pulmonary vein.

The coil of the positioning mechanism 14''' functions to anchor the elongate member 12 with respect to the anatomical structure, preferably a pulmonary vein 3000, by coupling to the anatomical structure. Preferably, the outward force of the coil against the interior wall of the pulmonary vein will hold the positioning mechanism 14''' within the pulmonary vein due to friction. The positioning mechanism 14''' may alternatively function to anchor the elongate member 12 with respect to the anatomical structure in any other suitable fashion.

Figure 12:
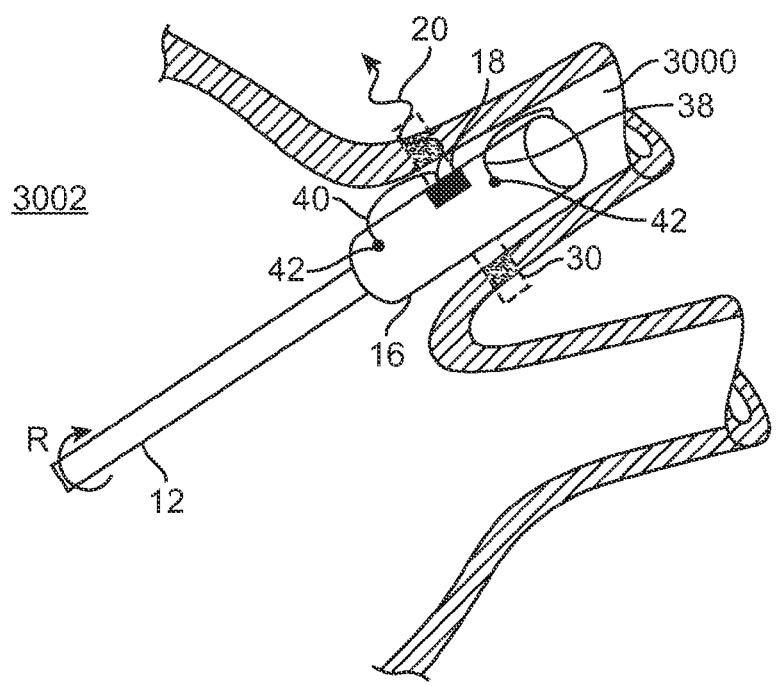
FIG. 12 is a drawing of a fifth variation of the positioning mechanism of the system of the preferred embodiment of the invention.

In a fifth variation, as shown in FIG. 12, the positioning mechanism includes at least one distal wire 38 and at least one proximal wire 40, each wrapped around at least a portion of the elongate member 12. The wires are preferably made from a conductive material and/or a material with shape memory such as nickel/titanium alloys or a shape memory polymer. The material is preferably flexible so as not to cause injury to the tissue of the heart where the wires might contact and move against it. At least a portion of each of the wires is preferably made from a fluoro-opaque material, such as platinum or gold, such that it may be seen while positioned inside the internal structures of a patient through the use of a fluoroscope. The fluoro-opaque portion is preferably located in any suitable position such that it may be seen while positioned inside the internal structures of a patient through the use of a fluoroscope. The fluoro-opaque portion is preferably flush with the wire, but may alternatively have a round or any other suitable shape such that it will not damage the tissue. Additionally, each of the wires preferably includes at least one electrically active portion 42 and/or at least one insulated portion (e.g. an insulating coating on a portion of each wire). The wires each preferably include an even number of electrically active portions 42 such that a bipolar electrical system may be used, wherein each pair of electrodes or electrically active portions has an opposite polarity. For clarity, only a single electrically active portion 42 per wire has been shown in FIG. 12. The wires may alternatively include a single electrode or electrically active portion and use a monopolar electrical system, or may include any other suitable number of electrodes or electrically active portions. The electrically active portion 42 is preferably located in any suitable position such that it comes in contact with tissue. The distal wire 38 is preferably located distally from the energy delivery structure 18, and the proximal wire is preferably located proximally from the energy delivery structure. The wires are preferably each coupled to the elongate member 12 at one end of the wire and then the other end is preferably wrapped around at least a portion of the elongate member 12 such that the other ends unwind towards the tissue once the distal tip assembly 16 is placed within the pulmonary vein 3000 or any other suitable structure. The wires preferably unwind such that the electrically active portion 42 of each wire is in contact with the tissue. The wires are preferably wrapped around the elongate member such that as the elongate member 12 and/or distal tip assembly are rotated (as shown by arrow R in FIG. 12), the electrically active portions 42 of the wires sweep along the tissue. The wires are further preferably wrapped around at least a portion of the elongate member such that they are biased away from one another. For example, the distal wire 38 may be wrapped such that the end is biased towards the distal end of the catheter. This will encourage the wires to not block the energy delivery structure and to not contact one another.

There is preferably at least one distal wire and at least one proximal wire such that, as the energy delivery structure 18 delivers energy to the tissue to form an ablation path and/or conduction block, there will be at least one wire distal to the conduction block and at least one wire proximal to the ablation path and/or conduction block.

Although omitted for conciseness, the preferred embodiments include every combination and permutation of the various elongate members 12 and positioning mechanism 14.

While the above is a complete description of the preferred embodiments of the invention, various alternatives, modifications, and equivalents may be used. Therefore, the above description should not be taken as limiting in scope of the invention which is defined by the appended claims.

What is claimed is:

1. A method of ablating an anatomic structure in a patient as a treatment for atrial fibrillation, said method comprising:
   providing an elongate shaft having a proximal end and a distal end;
   locating the anatomic structure with a positioning mechanism disposed adjacent the distal end of the shaft;
   anchoring the shaft with the positioning mechanism adjacent the anatomic structure;
   electrically stimulating or sensing electrical signals from the anatomic structure with an electrode disposed adjacent a distal portion of the positioning mechanism;
   delivering energy to the anatomic structure with an energy delivery element housed within an energy delivery structure disposed near a distal end of the shaft, and without contacting the anatomic structure with the energy delivery structure and the energy delivery element disposed therein, thereby creating a zone of ablation having a plurality of tissue points, that blocks abnormal electrical activity in order to reduce or eliminate atrial fibrillation in the patient; and
   moving the energy delivery structure along an ablation path while delivering energy with the energy delivery element, without contacting the anatomic structure with the energy delivery structure and the energy delivery element disposed therein;
   wherein the step of delivering energy further comprises modulating frequency, bandwidth, or amplitude of the energy delivered to the anatomic structure to compensate for known differences in distances between each of the plurality of tissue points in the zone of ablation and the energy delivery element, and
   wherein the energy is ultrasound energy.

2. The method of claim 1, wherein the elongate shaft comprises a lumen extending between the proximal and distal ends, the method further comprising delivering a fluid from the lumen to the anatomic structure.

3. The method of claim 1, wherein the step of locating the anatomic structure comprises visualizing the anatomic structure.

4. The method of claim 1, wherein the step of locating the anatomic structure comprises tactile or audible feedback.

5. The method of claim 1, wherein the step of locating the anatomic structure comprises advancing the positioning mechanism from, or retracting the positioning mechanism into the elongate shaft.

6. The method of claim 1, wherein the positioning mechanism comprises a plurality of wires and the step of locating the anatomic structure comprises deflecting at least some of the plurality of wires.

7. The method of claim 1, wherein the step of locating the anatomic structure comprises determining an entry angle of the elongate shaft into the anatomic structure.

8. The method of claim 1, wherein the step of anchoring the shaft comprises engaging the positioning mechanism against the anatomical structure and exerting an outward biasing force against an interior surface of the anatomical structure.

9. The method of claim 1, wherein the step of anchoring the shaft comprises forming and engaging a cage-like structure on the positioning mechanism with the anatomic structure.

10. The method of claim 1, wherein the step of stimulating the anatomic structure comprises stimulating in a monopolar mode.

11. The method of claim 1, wherein the step of stimulating the anatomic structure comprises stimulating in a bipolar mode.

12. The method of claim 1, wherein the step of stimulating the anatomic structure comprises pacing the patient's heart.

13. The method of claim 1, wherein the step of creating the zone of ablation comprises creating an acruate ablation path.

14. The method of claim 1, wherein the step of creating the zone of ablation comprises creating an ablation path around more than one pulmonary vein.

15. The method of claim 1, wherein the step of delivering energy comprises rotating the elongate shaft around the positioning mechanism.

16. The method of claim 1, wherein the step of creating the zone of ablation comprises creating a linear ablation path.

17. The method of claim 1, wherein the step of delivering energy comprises delivering energy through a window in the elongate shaft.

18. The method of claim 1, wherein the step of delivering energy comprises directing the energy along a path such that the path and a surface of the anatomic structure form an angle between 65 and 115 degrees.

19. The method of claim 1, wherein the anatomic structure comprises a pulmonary vein.

20. The method of claim 1, further comprising cooling the anatomic structure with cooling fluid.

21. The method of claim 1, wherein modulating comprises adjusting the energy to use less power for a first portion of the anatomic structure that is closer to the energy delivery element than a second portion of the anatomic structure.

22. The method of claim, wherein moving the energy delivery structure comprises actuating the elongate shaft to move the energy delivery structure along an ablation path, wherein actuating the elongate shaft comprises bending the shaft, moving the shaft linearly, or rotating the shaft about an axis.

23. The method of claim 1, wherein moving the energy delivery structure comprises moving the energy delivery structure while maintaining a substantially constant distance between the energy delivery structure and each of the plurality of tissue points in the zone of ablation.

24. A method of ablating a target tissue adjacent an anatomic structure of a patient as a treatment for atrial fibrillation, said method comprising:
provding an elongate shaft having a proximal end and a distal end;
locating the anatomic structure with a positioning mechanism disposed adjacent the distal end of the shaft;
anchoring the shaft with the positioning mechanism adjacent the anatomic structure;
electrically stimulating or sensing electrical signals from the anatomic structure with an electrode disposed adjacent a distal portion of the positioning mechanism;
delivering energy to the target tissue with an energy delivery element housed within an energy delivery structure disposed near the distal end of the shaft, without contacting the target tissue with the shaft or any other structure disposed thereon, thereby creating a zone of ablation having a plurality of tissue points, that blocks abnormal electrical activity in order to reduce or eliminate atrial fibrillation in the patient; and
moving the energy delivery structure along an ablation path while delivering energy with the energy delivery element, without contacting the target tissue with the shaft or any other structure disposed thereon.

25. The method of claim 24, wherein moving the energy delivery structure comprises actuating the elongate shaft to move the energy delivery structure along an ablation path, wherein actuating the elongate shaft comprises bending the shaft, moving the shaft linearly, or rotating the shaft about an axis.

26. The method of claim 24, wherein moving the energy delivery structure comprises moving the energy delivery structure while maintaining a substantially constant distance between the energy delivery structure and each of the plurality of tissue points in the zone of ablation.

* * * * *